(12) United States Patent  (10) Patent No.: US 9,009,862 B2
Huh  (45) Date of Patent: Apr. 21, 2015

(54) WELDING HELMET EQUIPPED WITH LIGHT SWITCHING WINDOW

(71) Applicant: Otos Wing Co., Ltd., Seoul (KR)

(72) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 23 days.

(21) Appl. No.: 14/025,067

(22) Filed: Sep. 12, 2013

(65) Prior Publication Data

US 2015/0067941 A1  Mar. 12, 2015

(51) Int. Cl.
  *A61F 9/06*  (2006.01)
(52) U.S. Cl.
  CPC ........................ *A61F 9/06* (2013.01)
(58) Field of Classification Search
  CPC .............................. A61F 11/06; A61F 11/061
  USPC ................... 2/8.3, 8.1, 8.5, 8.2, 8.7
  See application file for complete search history.

(56) References Cited

U.S. PATENT DOCUMENTS

| | | | | |
|---|---|---|---|---|
| 1,497,012 A | * | 6/1924 | Goodspeed | 219/147 |
| 2,086,208 A | * | 7/1937 | Brekelbaum | 2/8.3 |
| 2,212,014 A | * | 8/1940 | Doyle | 2/8.1 |
| 2,270,238 A | * | 1/1942 | Clarke et al. | 2/6.2 |
| 2,384,765 A | * | 9/1945 | O'Reilly | 2/8.3 |
| 2,411,224 A | * | 11/1946 | O'Reilly | 2/8.3 |
| 2,693,597 A | * | 11/1954 | Horlbeck | 2/8.3 |
| 3,278,943 A | * | 10/1966 | Manz | 2/8.3 |
| 3,368,220 A | * | 2/1968 | Wenzel | 2/8.3 |
| 3,768,099 A | * | 10/1973 | Manz | 2/8.3 |
| 4,039,254 A | * | 8/1977 | Harsch | 349/14 |
| 4,646,363 A | * | 3/1987 | Wood | 2/8.5 |
| 5,140,707 A | * | 8/1992 | Johnson | 2/8.1 |
| 5,191,468 A | * | 3/1993 | Mases | 359/361 |
| 5,561,855 A | * | 10/1996 | McFall | 2/8.6 |
| 6,008,466 A | * | 12/1999 | Hosoda | 219/121.62 |
| 6,151,711 A | * | 11/2000 | Edwards | 2/8.3 |
| 2007/0089216 A1 | * | 4/2007 | Walkden | 2/8.7 |
| 2008/0158502 A1 | * | 7/2008 | Becker et al. | 351/44 |
| 2011/0023204 A1 | * | 2/2011 | Brace | 2/8.2 |
| 2011/0247119 A1 | * | 10/2011 | Cheng | 2/8.5 |

* cited by examiner

*Primary Examiner* — Richale Quinn
(74) *Attorney, Agent, or Firm* — Cantor Colburn LLP

(57) ABSTRACT

Disclosed herein is a welding helmet in which a worker may transmit and block external light as necessary by forming a light switching window for blocking external light from a side surface of the welding helmet (helmet). The welding helmet equipped with a light switching window, which includes a helmet body portion which protects the worker's face and a cartridge which blocks harmful light generated during welding to protect the worker's eyes, includes a light switching window formed on a side surface of the helmet body portion such that external light is transmitted or blocked by the light switching window. The light switching window has a structure in which it may be possible to identify risk factors around a work area and a worker may block unnecessary light as necessary. Particularly, since an operating radius is enlarged, it may be possible to provide the worker with convenience.

3 Claims, 6 Drawing Sheets

WELDING HELMET EQUIPPED WITH LIGHT SWITCHING WINDOW

BACKGROUND OF THE INVENTION

1. Field of the Invention

The present invention relates to a welding helmet equipped with a light switching window, and more particularly to a welding helmet in which a worker may transmit and block external light as necessary by forming a light switching window for blocking external light from a side surface of the welding helmet (including a welding mask, etc.).

2. Description of the Related Art

In general, arc welding involves locally heating and melting metals using fusibility of metals to join the metals together. A worker wears a welding helmet as a representative example of protective equipment for protecting oneself from high heat, light, and gas generated during welding.

Particularly, the welding helmet is used to protect the worker's eyes and face when performing tasks such as welding or cutting. An anti-glare device (hereinafter, referred to as a "cartridge") is fixedly mounted to the welding helmet, in order to protect the worker's eyes from intense harmful light generated when performing tasks such as welding or cutting.

Such a cartridge generally blocks light of wavelengths greater than 780 nm (IB) and less than 365 nm (UV) and controls transmittance of visible light, thereby allowing the worker to perform work while viewing welding locations without exposure to glare.

Conventionally, the welding helmet formed at the side surface thereof with a semitransparent window is used. However, since this welding helmet is always exposed to external light, there is a problem in that the external light hinders the worker from working or worker concentration is deteriorated when it is too bright.

SUMMARY OF THE INVENTION

Therefore, the present invention has been made in view of the above problems, and it is an object of the present invention to provide a welding helmet formed with a light switching window on a side surface thereof so as to transmit or block external light to or from the side surface of the welding helmet.

In accordance with the present invention, the above and other objects can be accomplished by the provision of a welding helmet equipped with a light switching window, which includes a helmet body portion which protects the worker's face and a cartridge which blocks harmful light generated during welding to protect the worker's eyes, including a light switching window formed on a side surface of the helmet body portion such that external light is conveniently transmitted or blocked by the light switching window.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Reference will now be made in detail to a welding helmet equipped with a light switching window according to the preferred embodiment of the present invention with reference to the attached drawings.

The terms or words used in the specification and claims of the present invention are not to be construed as limited to ordinary or dictionary meanings, but should be construed as meanings and concepts conforming to the technical spirit of the present invention on the basis of the principle that the inventors can define the concept of the terms properly to explain their invention with the best method.

Accordingly, it is to be understood that the detailed description which will be disclosed along with the accompanying drawings is intended to describe an exemplary embodiment of the present invention, and is not intended to describe a unique embodiment which the present invention can be carried out. Therefore, various equivalents and modifications are possible within the scope of the present invention at the time of filing.

Figure 1:
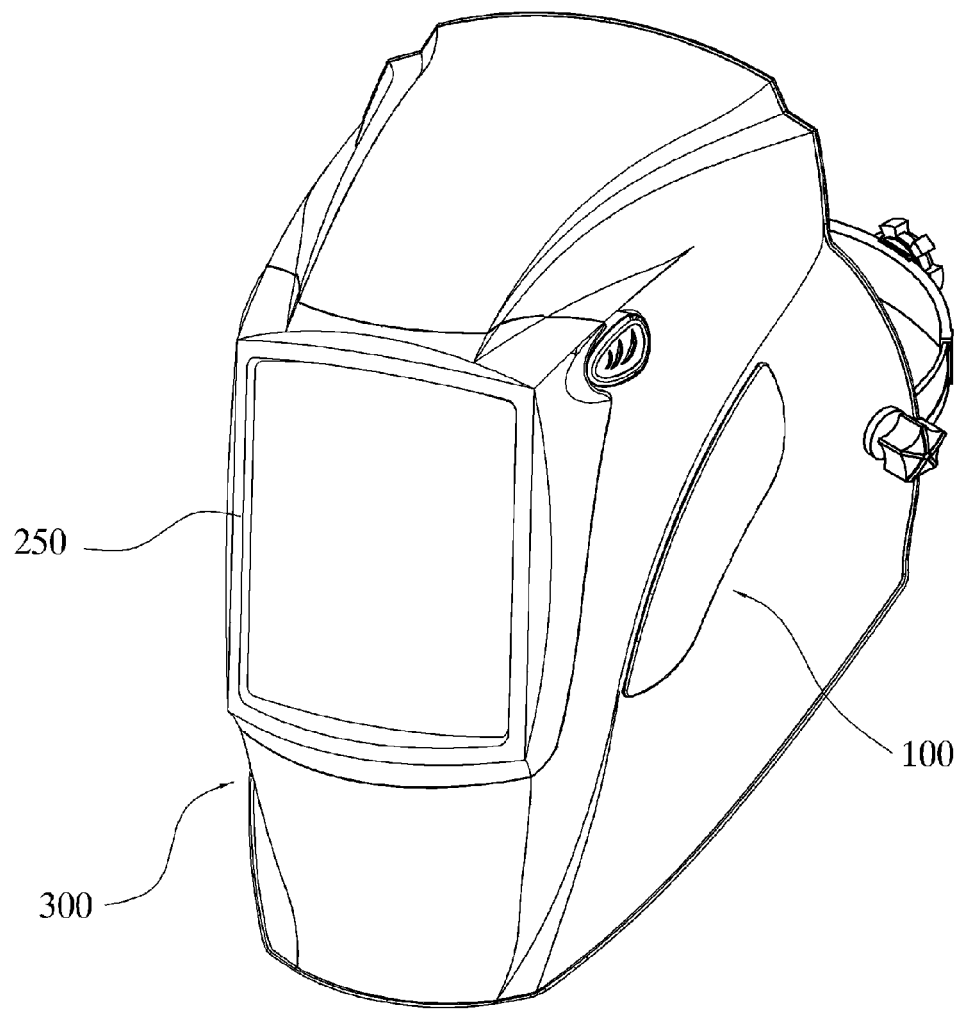
FIG. 1 is a perspective view illustrating a welding helmet equipped with a light switching window according to an embodiment of the present invention.
Figure 2:
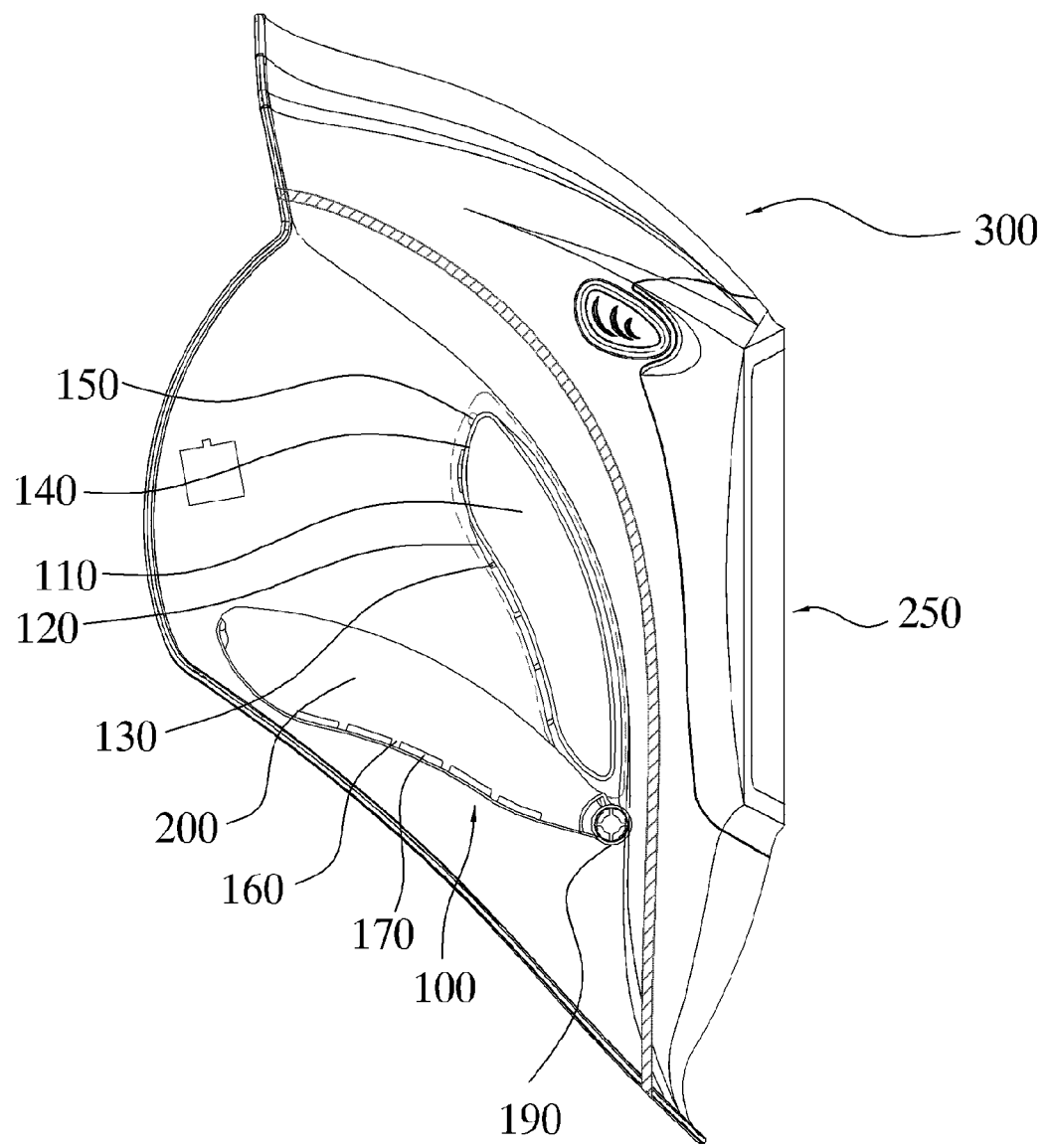
FIG. 2 is a cut perspective view illustrating a portion of the welding helmet equipped with a light switching window according to the embodiment of the present invention.
Figure 3:
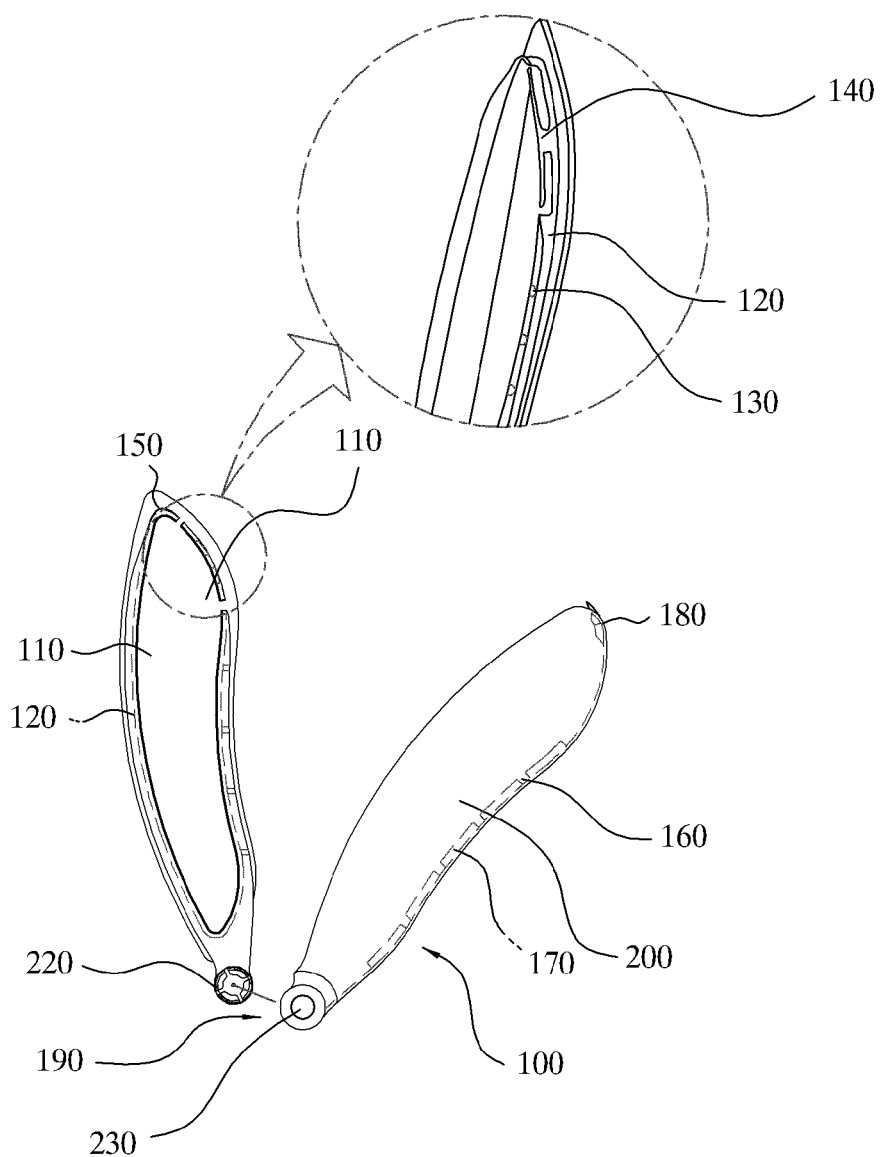
FIG. 3 is an exploded perspective view illustrating a light switching window according to the embodiment of the present invention.
Figure 4:
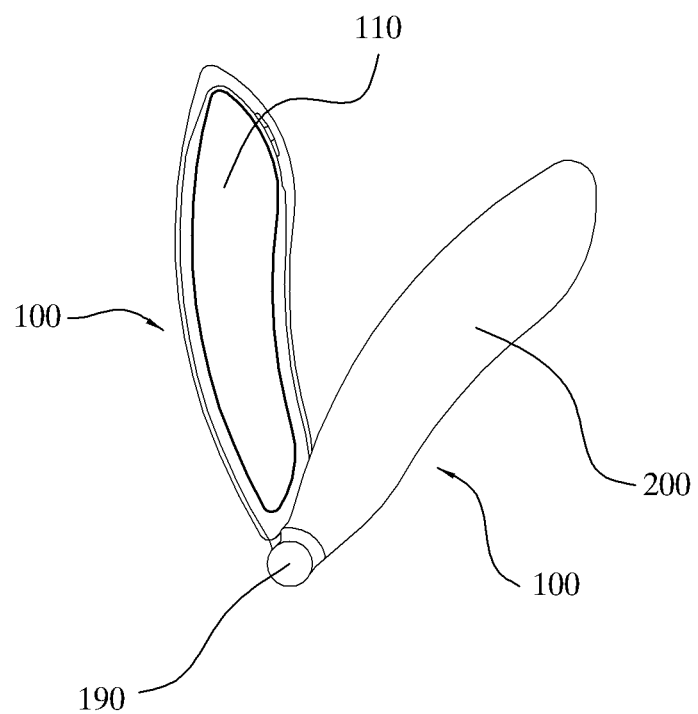
FIG. 4 is a coupled perspective view illustrating the light switching window according to the embodiment of the present invention.
Figure 5:
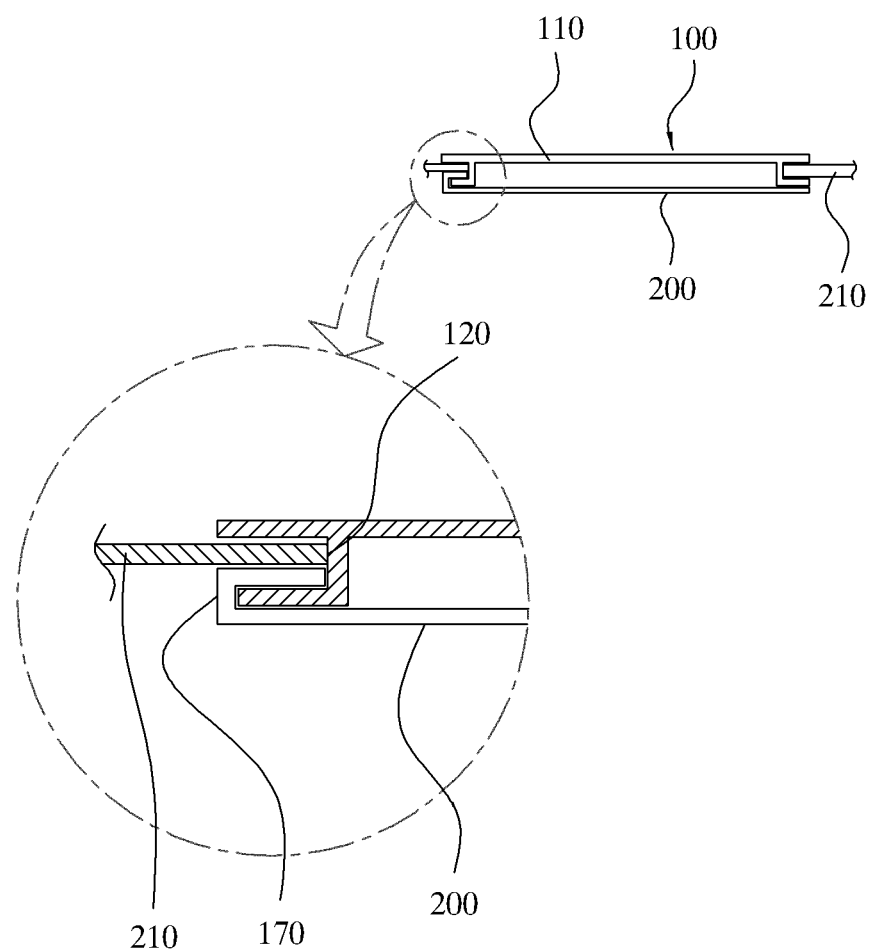
FIG. 5 is a cross-sectional view illustrating the welding helmet equipped with a light switching window according to the embodiment of the present invention.
Figure 6:
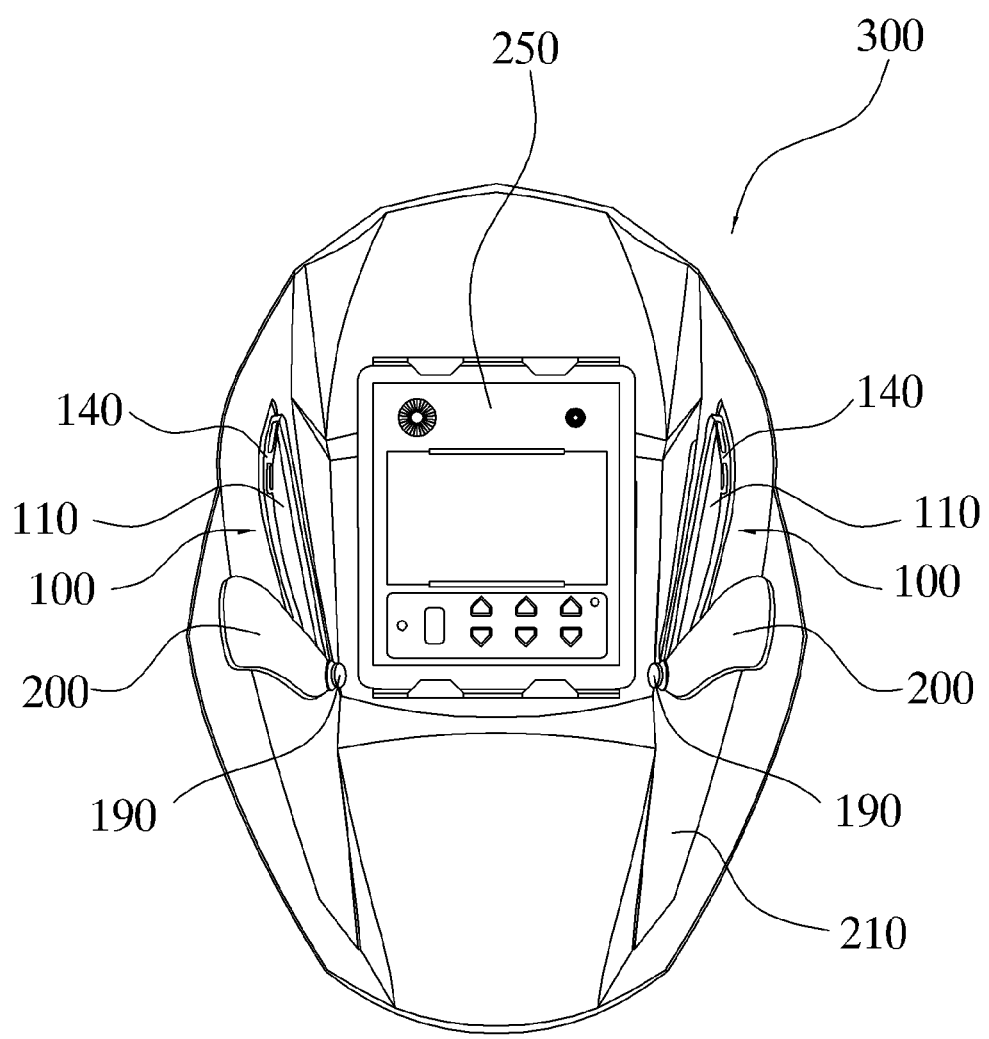
FIG. 6 is an in-use view of the welding helmet equipped with a light switching window according to the embodiment of the present invention.

FIGS. 1 to 6 show a welding helmet 300 of the present invention including a helmet body portion 210 which covers and protects the worker's face and a cartridge 250 which blocks harmful light to protect the worker's eyes during welding.

In the welding helmet 300, a coupling structure is provided in which light switching windows 100 are formed on opposite side surfaces of the helmet body portion 210 such that external light is transmitted or blocked by the light switching windows 100.

In accordance with the present invention, since the light switching windows 100 are formed on the opposite side surfaces of the helmet body portion 210, it may be possible to identify risk factors around a work area and prevent safety accidents. In addition, since a worker's operating radius is enlarged, it may be possible to prevent worker uneasiness.

Each of the light switching windows 100 includes a semitransparent window 110 and a light switching cover 200, which are formed as follows, so as to be coupled to each other.

The semitransparent window 110 is formed, at an edge surface thereof, with a fitting groove 120 so as to be fixedly fitted in the helmet body portion 210 of the welding helmet. The semitransparent window 110 is formed, at a tip end thereof, with an axial protrusion 220 about which the light switching cover 200 is rotatable. An axial portion 190 is formed in which the axial protrusion 220 is fitted and coupled in an axial groove 230 formed at a tip end of the light switching cover 200.

Respective tip ends of the semitransparent window 110 and the light switching cover 200 which are opposite to the axial portion 190 are formed with a hook 150 and a lock groove 180 for pressing the tip ends against each other, so that the tip ends are pressed against each other during closing of the light switching cover 200.

According to this configuration, the light switching cover 200 is rotated about the axial portion 190, thereby enabling external light to be transmitted or blocked.

In addition, the fitting groove 120 is formed along the entire edge surface of the semitransparent window 110 such that the semitransparent window 110 may be fitted and mounted in the helmet body portion 210. A portion of the fitting groove is formed as an elastic piece 140 such that, when the semitransparent window 110 is pushed and fitted in the helmet body portion using the fitting groove and then a remaining portion of the semitransparent window is forcibly inserted, the remaining portion is not withdrawn after insertion.

A plurality of pressing groves 160 are formed between the fitting groove 120 of the semitransparent window 110 and a catching portion 170 of the light switching cover 200 which is pressed against the fitting groove. In addition, pressing protrusions 130 formed in the fitting groove are fitted in the pressing groves 160 to be pressed against each other, so that the light switching cover is coupled to the semitransparent window so as not to be easily withdrawn therefrom.

The light switching cover 200 is formed such that one side surface thereof does not have the catching portion and the other side surface has the catching portion 170. Accordingly, when an upper surface of the semitransparent window is covered by the light switching cover in a sliding manner, the surface of the light switching cover absent the catching portion easily slides and the catching portion formed at an end surface of the light switching cover is caught by the fitting groove of the semitransparent window. Consequently, the semitransparent window coincides with the light switching cover in an overlapping fashion.

In accordance with the welding helmet equipped with a light switching window having the above-mentioned configurations, the worker may conveniently utilize the light switching window for transmitting or blocking light during work.

Particularly, in accordance with the present invention, it may be possible to block unnecessary light by formation of the light switching window 100, and to enhance work efficiency by opening the light switching window during work and relieving worker uneasiness.

As is apparent from the above description, in accordance with a welding helmet equipped with a light switching window, first, it may be possible to identify risk factors around a work area. Secondly, it may be possible to enlarge an operating radius. Thirdly, it may be possible to prevent worker uneasiness by formation of the light switching window. Fourthly, it may be possible to block unnecessary light by formation of the light switching window. Fifthly, it may be possible to prevent worker uneasiness during work by opening the light switching window. Furthermore, since the light switching window may block external light, it may be possible to enhance worker concentration and prevent worker disorientation due to diffused reflection.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A welding helmet equipped with a light switching window, including a helmet body portion which protects the worker's face and a cartridge which blocks harmful light generated during welding to protect the worker's eyes, comprising:
    a light switching window formed on a side surface of the helmet body portion such that external light is transmitted or blocked by the light switching window,
    wherein the light switching window comprises a semitransparent window and a light switching cover, the semitransparent window is formed, at a tip end thereof, with an axial protrusion, and an axial portion, in which the axial protrusion is fitted and coupled in an axial groove formed at a tip end of the light switching cover, is formed such that the light switching cover is rotatable about the axial portion.

2. The welding helmet equipped with a light switching window according to claim 1, wherein the light switching window is formed on one surface or both surfaces of the helmet body portion.

3. The welding helmet equipped with a light switching window according to claim 1, wherein the light switching window has a fitting groove formed at a side surface of a semitransparent window so as to be fitted and coupled in a side through hole of the helmet body portion through the fitting groove.

* * * * *